US012667700B2

(12) United States Patent
Chelak et al.

(10) Patent No.: US 12,667,700 B2
(45) Date of Patent: Jun. 30, 2026

(54) IV CATHETER STABILIZATION AND INTERROGATION DEVICE AND METHOD

(71) Applicant: NP Medical Inc., Clinton, MA (US)

(72) Inventors: Todd Chelak, Pelham, NH (US); John Damarati, Marlborough, MA (US)

(73) Assignee: NP Medical Inc., Clinton, MA (US)

( * ) Notice: Subject to any disclaimer, the term of this patent is extended or adjusted under 35 U.S.C. 154(b) by 559 days.

(21) Appl. No.: 18/032,830

(22) PCT Filed: Oct. 28, 2020

(86) PCT No.: PCT/US2020/057745
§ 371 (c)(1),
(2) Date: Apr. 20, 2023

(87) PCT Pub. No.: WO2022/093215
PCT Pub. Date: May 5, 2022

(65) Prior Publication Data
US 2023/0390528 A1    Dec. 7, 2023

(51) Int. Cl.
*A61M 25/02*    (2006.01)
*A61M 99/00*    (2012.01)

(52) U.S. Cl.
CPC ....... *A61M 25/02* (2013.01); *A61M 2025/024* (2013.01); *A61M 99/00* (2022.08); *A61M 2205/3368* (2013.01)

(58) Field of Classification Search
CPC .................. A61M 25/02; A61M 99/00; A61M 2025/024; A61M 2205/3368;
(Continued)

(56) References Cited

U.S. PATENT DOCUMENTS

| | | | |
|---|---|---|---|
| 2002/0107436 A1* | 8/2002 | Barton | ................. A61B 5/0008 |
| | | | 600/382 |
| 2011/0071482 A1 | 3/2011 | Selevan | |

(Continued)

FOREIGN PATENT DOCUMENTS

| | | |
|---|---|---|
| EP | 3473291 A1 | 4/2019 |
| JP | 2020-036935 A | 3/2020 |
| WO | 2020/005705 A1 | 1/2020 |

OTHER PUBLICATIONS

International Search Report and Written Opinion for Application No. PCT/US2020/057745, dated Jul. 28, 2021, 9 pages.

*Primary Examiner* — Theodore J Stigell
(74) *Attorney, Agent, or Firm* — McCarter & English, LLP; Jonathan C. Lovely

(57) ABSTRACT

A catheter stabilization and interrogation device includes a flexible substrate with a proximal portion, a distal portion spaced from the proximal portion, and an intermediate portion located, at least partially, between the proximal portion and the distal portion. The intermediate portion conforms to a patients body, and a bottom surface of the substrate has an adhesive to secure the device to a patient. A stabilizer secured to the proximal portion stabilizes the catheter relative to the patients vasculature and a receptacle located within and/or upon the distal portion receives an interacting element and positions the interacting element relative to the catheter. A monitoring device, constructed within at least the intermediate portion, monitors at least one event within the patient.

19 Claims, 10 Drawing Sheets

(58) Field of Classification Search
CPC .. A61M 2005/1586; A61M 2005/1588; A61M
2025/028; A61M 2205/053; A61M
2205/054; A61B 5/6833; A61B
2560/0276; A61B 2560/0412; A61B 5/01;
A61B 5/4839
See application file for complete search history.

(56) References Cited

U.S. PATENT DOCUMENTS

| | | | |
|---|---|---|---|
| 2019/0091447 A1 | 3/2019 | Albany et al. | |
| 2019/0117297 A1 | 4/2019 | Beeckler et al. | |
| 2019/0358387 A1 | 11/2019 | Elbadry et al. | |
| 2019/0388652 A1* | 12/2019 | Albany | A61M 25/02 |
| 2020/0330733 A1 | 10/2020 | Howell | |

\* cited by examiner

IV CATHETER STABILIZATION AND INTERROGATION DEVICE AND METHOD

TECHNICAL FIELD

The present invention relates to vascular access site management systems, and more particularly to systems and methods for stabilizing indwelling IV catheters and monitoring IV therapy.

BACKGROUND ART

In instances in which a patient will need regular administration of fluid or medications (or regular withdrawal of fluids/blood), catheters are often inserted into a vein of the patient and used to administer the fluids/medications. The catheter may remain in the patient for extended periods of time (e.g., several days). Additionally, an extension tube may be connected to the catheter to facilitate use of the catheter and connection of a medical implement (e.g., a syringe). To ensure that the catheter and/or extension tube remain in place and are not accidentally removed, some prior art systems secure the catheter and/or extension tube to the patient using adhesive materials (e.g., a film-based securement dressing or a mechanical securement device).

Securement dressings and devices can be problematic in that they may not secure the catheter in place for the desired period of time. Additionally, in some instances, the manner in which the dressing or device is applied and the positioning/location of the catheter and/or extension tube may cause the catheter and/or extension tube to be bent or the catheter to piston within the vein. This, in turn, increases the risk of kinking (which can reduce/stop flow through the catheter and/or extension tube) or catheter dislodgment from the vein and makes it more difficult to deliver the fluid/medication. Furthermore, securing using adhesive material provides no feedback to the user regarding the efficacy of IV therapy.

SUMMARY OF THE INVENTION

In accordance with one embodiment of the invention, a catheter stabilization and interrogation device includes a flexible substrate having a proximal portion, a distal portion spaced from the proximal portion, and an intermediate portion located, at least partially, between the proximal portion and the distal portion. The substrate may conform to a patient's body, and a bottom surface of the substrate may have an adhesive that secures the device to a patient. The device may also have a stabilizer secured to the proximal portion and a receptacle located within and/or upon the distal portion. The stabilizer may stabilize the catheter relative to the patient's vasculature when the device is secured to the patient. The receptacle may receive an interacting element and position the interacting element relative to the catheter. A monitoring device constructed within at least the intermediate portion may monitor at least one event within the patient. The at least one event may be along a length of and/or adjacent to the catheter and may include IV therapy, infiltration/extravasation of fluid, catheter dislodgment from the vein, phlebitis, local infection, systemic infection, and/or blockage of flow.

In some embodiments, the device may have a tube clip located within the proximal portion that secures a tube from a connector set connected to the catheter. Additionally or alternatively, the stabilizer may receive a portion of the catheter to stabilize the catheter and/or set an angle of the catheter relative to the patient. The proximal portion and/or the distal portion may be axially aligned with the catheter.

The intermediate portion may be a dielectric portion with electronics printed and/or mounted thereon. For example, the electronics may include a first temperature sensor located nearer the proximal portion and a second temperature sensor located nearer the distal portion. The first temperature sensor may monitor a first temperature at a first point along a length of the catheter, and the second temperature sensor may monitor a second temperature at a second point along the length of the catheter. The first point along the length of the catheter may be at an insertion site of the catheter and the second point along the length of the catheter may be at the tip of the catheter. The electronics may include an antenna and/or the interacting element may be a sensor probe (e.g. a photoplethysmography sensor). Additionally or alternatively, the interacting element may provide a stimulus to a vein and/or the area surrounding the vein in which the catheter is inserted. The stimulus may be a mechanical stimulus, a thermal stimulus, an acoustic pressure stimulus, an electromagnetic stimulus, a chemical stimulus, and/or an electrical stimulus.

In accordance with additional embodiments of the present invention, a method for monitoring at least one event within a body of a patient includes providing a catheter stabilization and interrogation device that includes a flexible substrate, a stabilizer, a receptacle, and a monitoring device. The flexible substrate may have a proximal portion, a distal portion spaced from the proximal portion, and an intermediate portion located, at least partially, between the proximal portion and the distal portion. The substrate and/or the intermediate portion may conform to a patient's body, and a bottom surface of the substrate may have an adhesive that secures the device to a patient. The stabilizer may be secured to the proximal portion and may stabilize the catheter relative to the patient's vasculature when the device is secured to the patient. The receptacle may be located within and/or upon the distal portion, may receive an interacting element (e.g., a sensor probe), and may position the interacting element relative to the catheter. The monitoring device may be constructed within at least the intermediate portion and may monitor at least one event within the patient. The method may include placing the catheter stabilization and interrogation device on the patient to allow the adhesive to secure the device to the patient, and connecting the catheter to the stabilizer to stabilize the catheter relative to the patient's vasculature. The method may then position the interacting element within the receptacle and monitor the at least one event within the patient.

The intermediate portion may be a dielectric portion with printed and/or mounted electronics on it. The electronics may include a first temperature sensor located nearer the proximal portion and a second temperature sensor located nearer the distal end. Monitoring the at least one event may include monitoring, using the first temperature sensor, a first temperature at a first point along a length of the catheter, and monitoring, using the second temperature sensor, a second temperature at a second point along the length of the catheter. For example, the first point may be at an insertion site of the catheter and the second point may be at the tip of the catheter. The at least one event may be along a length of and/or adjacent to the catheter. The method may also include sending, using an antenna located on the catheter stabilization and interrogation device, data from the monitoring device to a remote device. The stabilizer may set an angle of the catheter relative to the patient.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, an IV catheter stabilization and interrogation device has various structural elements that facilitate the assessment of an indwelling IV catheter and patient during IV Therapy while helping preserve catheter functionality over its useful life. The device may conform/attach to the patient's body at the IV catheter insertion site (e.g. arm, hand) and may be applied to the body subsequent to successful insertion of the catheter into the vasculature.

Figure 1:
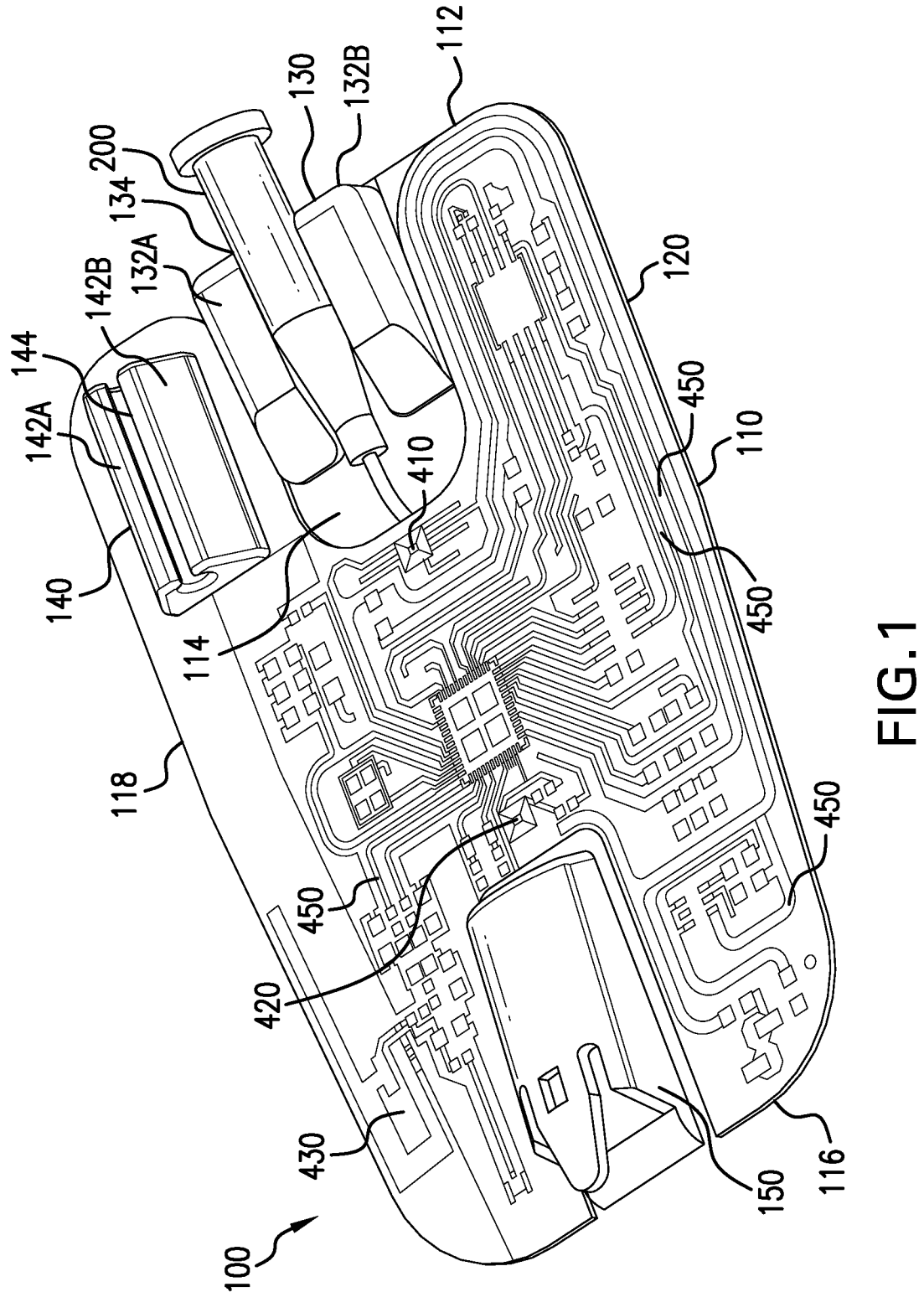
FIG. 1 schematically shows a perspective view of an IV catheter stabilization and interrogation device in accordance with various embodiments of the present invention.
Figure 2:
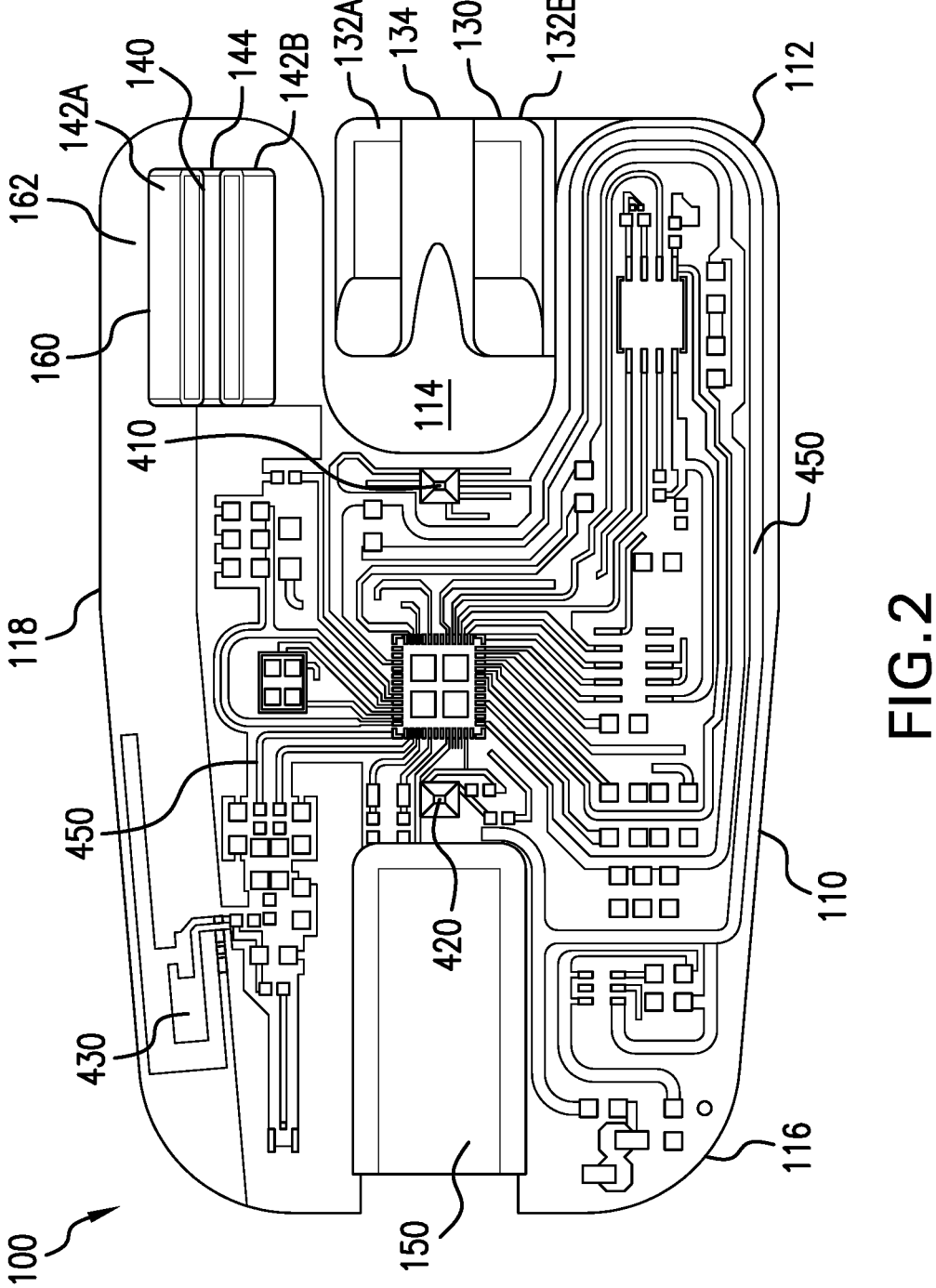
FIG. 2 schematically shows a top view of the IV catheter stabilization and interrogation device shown in FIG. 1, in accordance with some embodiments of the present invention.
Figure 3A:
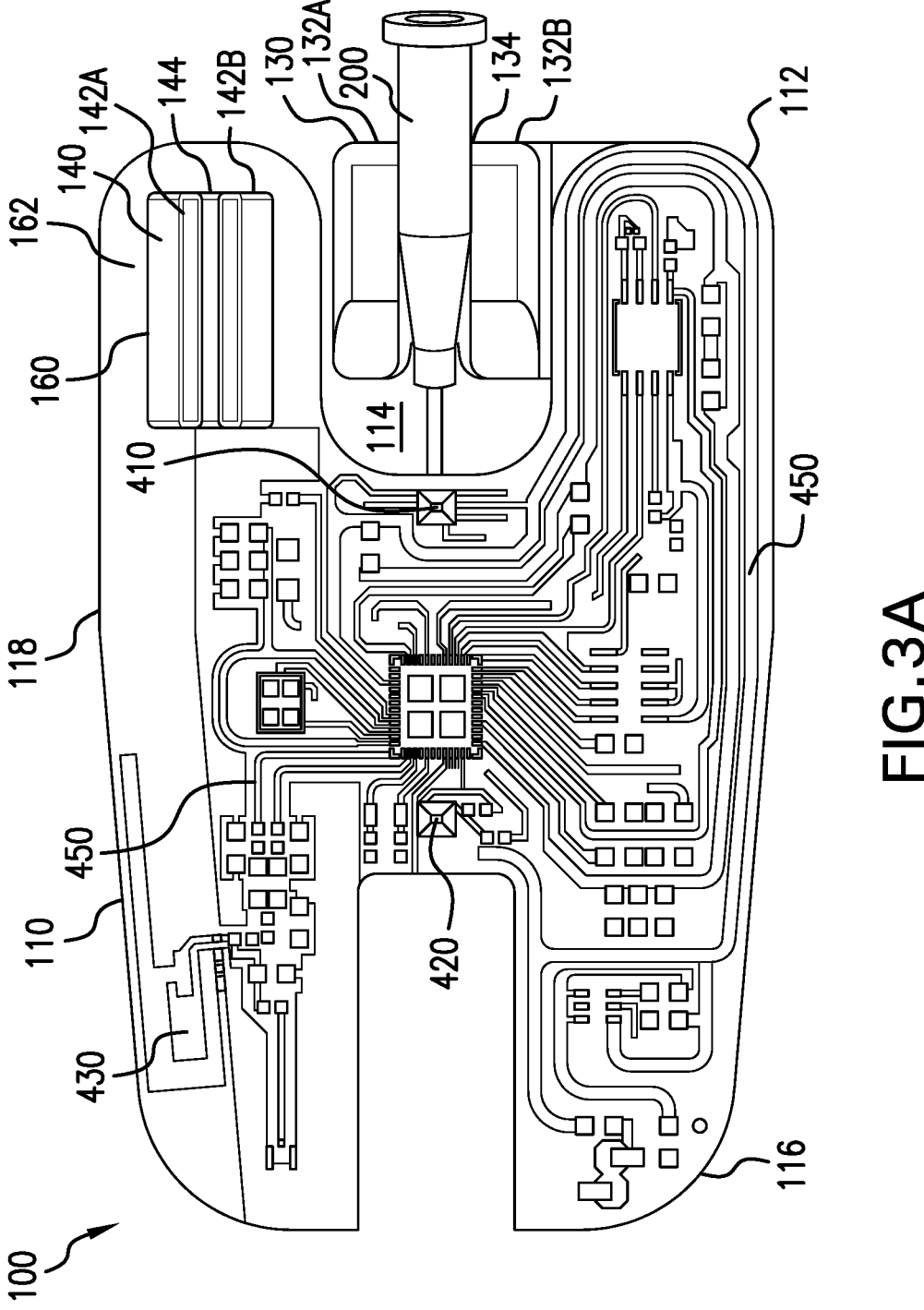
FIGS. 3A-3D schematically show various views of an IV catheter stabilization and interrogation device, in accordance with additional embodiments of the present invention.
Figure 3B:
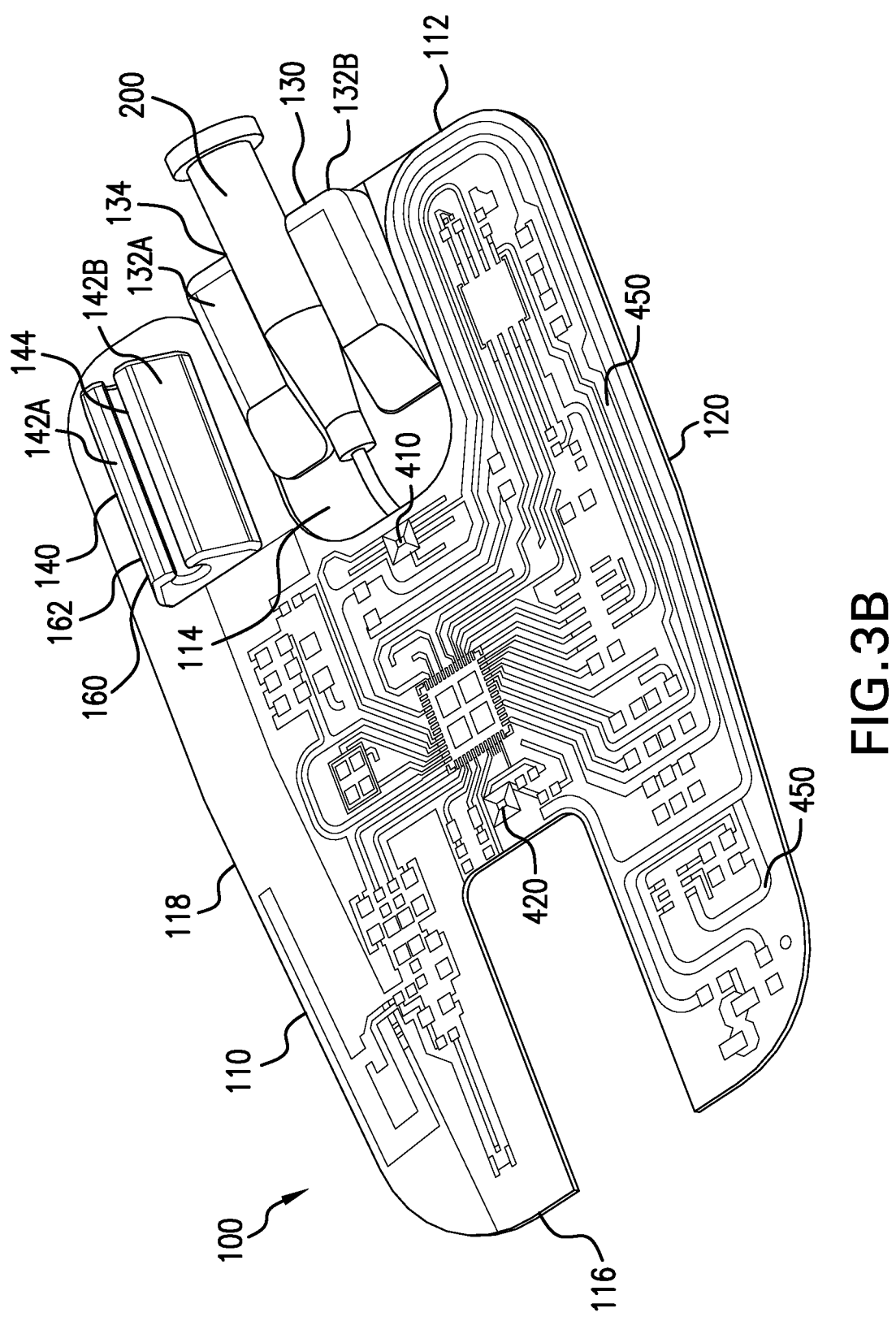
Figure 3C:
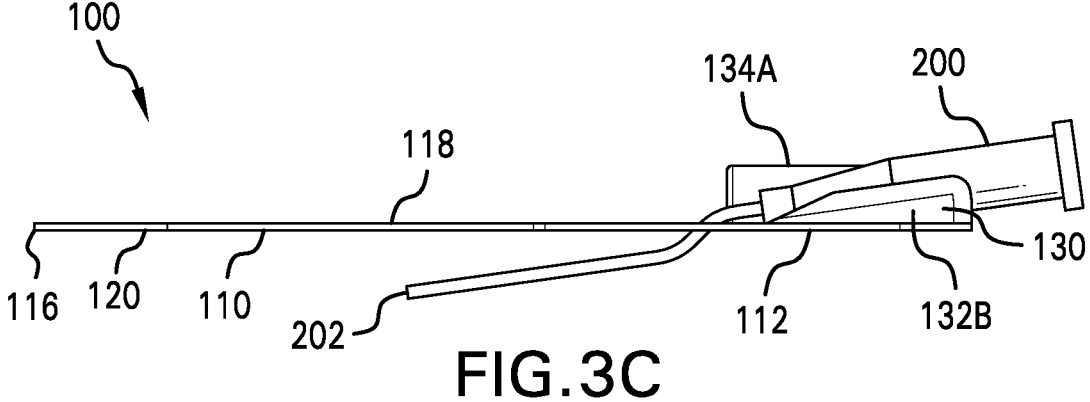
Figure 3D:
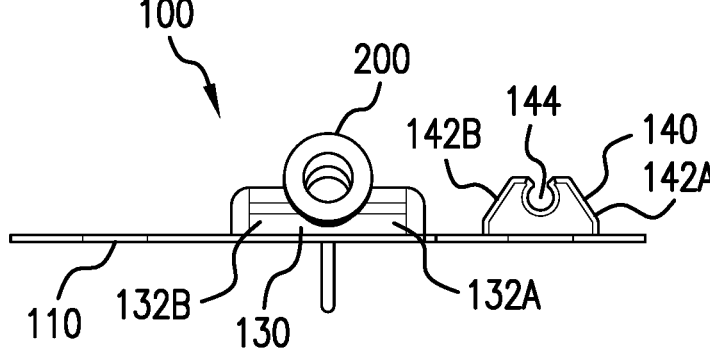

FIGS. 1 and 2 schematically show a perspective view and a top view of a catheter stabilization and interrogation device 100 in accordance with some embodiments of the present invention. The stabilization device 100 may include a substrate 110 that may be applied to the patient 350 (e.g., the arm of the patient). More specifically, the substrate 110 may include an adhesive layer 120 (e.g., pressure-sensitive, medical grade adhesive) on its underside to secure the stabilization device 100 to the patient 350. Although any number of adhesives may be used to secure the stabilization device 100 to the patient 350 (e.g. acrylic, hydrocolloid, hydrogel, PU gel, silicone gel), the adhesive should be strong enough such that the substrate 110 and the stabilization device 100 do not peel off the patient's skin during regular movement by the patient 350 (e.g., manipulation of the hand, arm etc.). To prevent the adhesive from accidentally sticking to the wrong surface prior to use, the device 100 may include a protective layer (not shown) that covers the adhesive and may be removed just prior to use. For patient comfort and to provide better securement, the substrate 110 (and any layers that make up the substrate 110) may be flexible so that the device 100 can conform to the contours of the patient's skin and allow for manipulation by the user when attaching the stabilization device 100 to the catheter 200. For example, the substrate 110 may be a film and can be made from any number of materials including, but not limited to polyurethane, polyester, polyethylene, and/or PVC.

To attach the catheter 200 to the device 100 and to allow the device 100 to stabilize the catheter 200, the device 100 includes a stabilizer 130 located nearer one end/portion (e.g., a proximal portion 112) of the substrate 110. For example, the stabilizer 130 may include raised portions 132A/B that define a recess/channel 134. After the catheter has been inserted into the patient 350 and the device 100 secured to the patient 350, the catheter 200 may be inserted into the recess/channel 134, where it may be generally held in place by the raised portions 132A/B. Alternatively, the catheter 200 may be attached to the stabilizer 130 prior to securing the device 100 to the patient 350. To allow the catheter 200 to extend through the substrate 110, the substrate 110 may include an opening 114 located in front of the stabilizer 130. In some embodiments, the stabilizer 130 and/or the channel 134 may be oriented at an angle to set an angle of the catheter 200 within the patient 350. Additionally, the stabilizer 130 may position the catheter 200 relative to the patient 350 and/or the patient's vasculature.

Also located on the proximal portion 112 of the substrate 110, the device 100 may have a tube clip 140 that receives a portion of the tubing of the IV tubing line 210 that may be connected to the catheter 200 (e.g., to allow fluid transfer into and out of the patient 350). Like the stabilizer 130, the tube clip 140 may include raised portions 142A/B that define a recess/channel 144. Before or after connecting the tubing line 210 to the catheter 200, the tubing 210 may be inserted into the recess/channel 144, where it may be held in place by the raised portions 142A/B. In addition to helping to secure the catheter 200 and tubing line 210 to the device 100, by holding the tubing line 210 in place, the tube clip 140 helps to prevent the tubing 210 from kinking or becoming twisted during use.

Figure 4A:
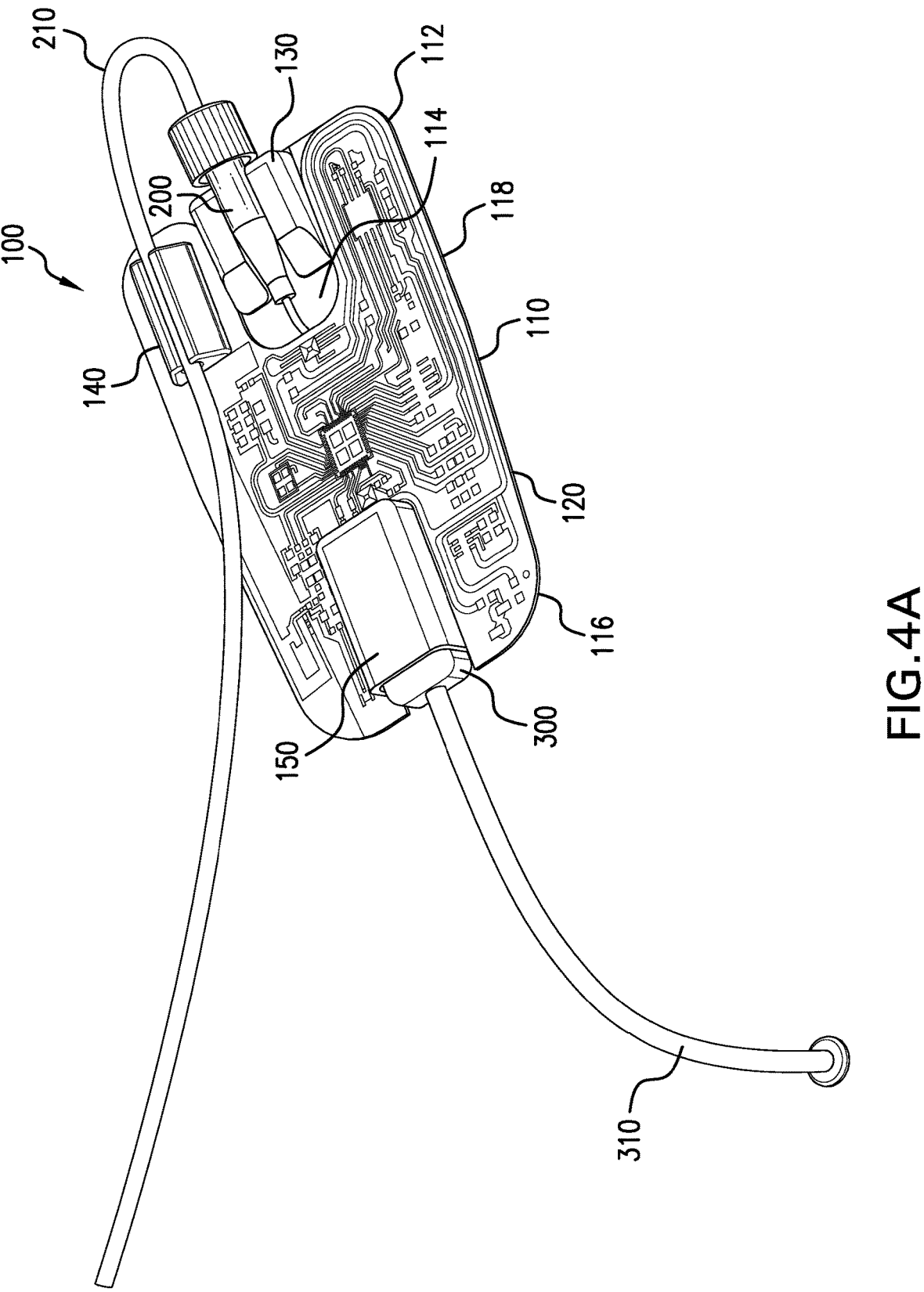
FIGS. 4A and 4B schematically show an IV catheter stabilization and interrogation device connected to a catheter and an interacting element/sensor probe, in accordance with various embodiments of the present invention.
Figure 4B:
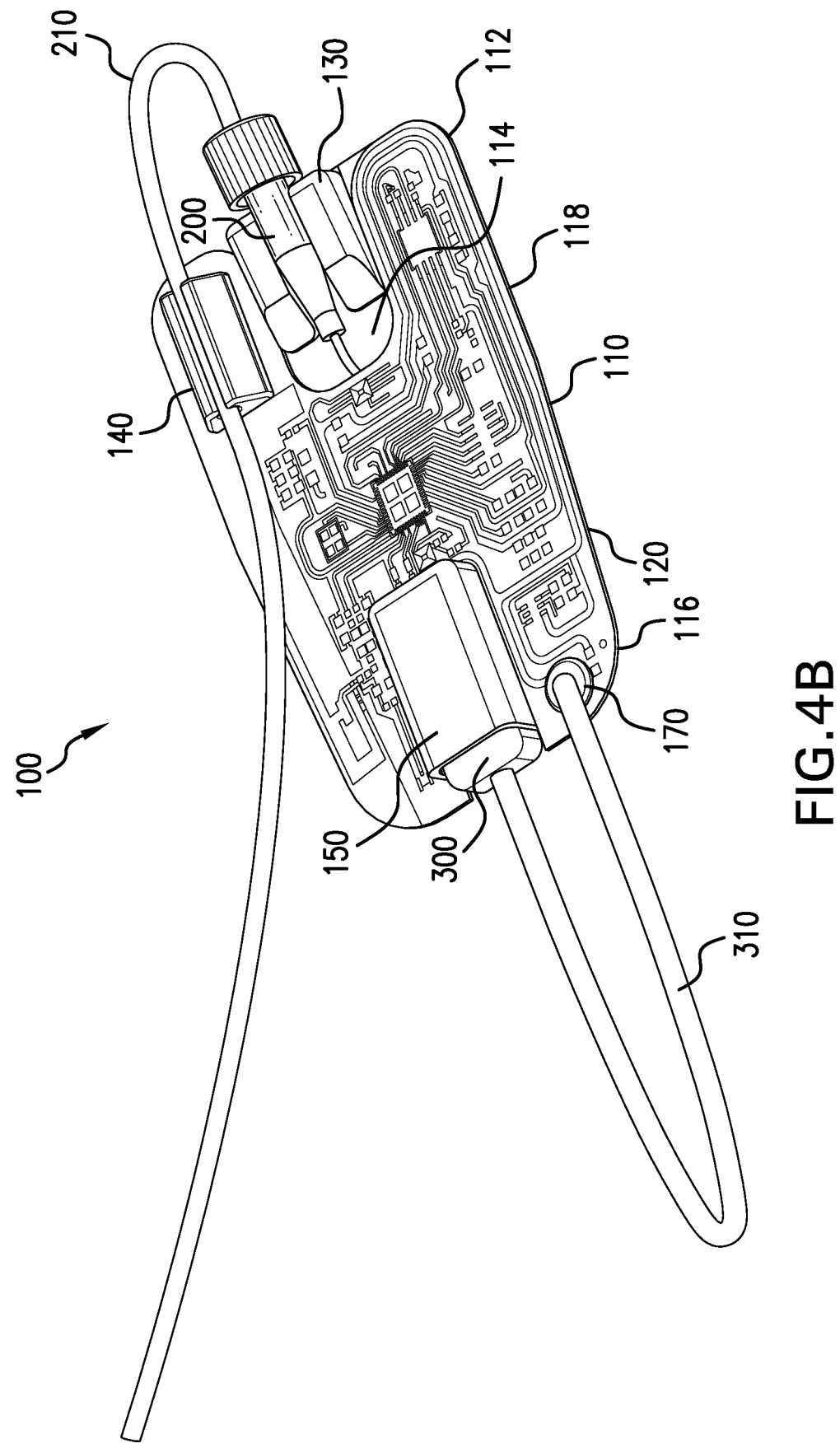

At the opposing end of the substrate 110 (e.g., within a distal portion 116 of the substrate 110), the device 100 may have a receptacle 150 that is located within and/or upon the substrate 110. As discussed in greater detail below, various embodiments of the present invention may monitor one or more events within the patient 350, for example, in relation to the IV therapy (e.g., infiltration/extravasation of fluid, catheter dislodgment from the vein, phlebitis, local infection, systemic infection, and blockage of flow). To that end, the receptacle 150 may receive an interacting element 300 (FIG. 4A, 4B) that interacts in some way with the patient 350 and/or IV therapy and may position the interacting element 300 relative to the tip of the catheter 200. For example, the interacting element 300 may be a sensing probe (e.g. a photoplethysmography sensor) that monitors one or more characteristics within the patient 350 and/or a condition of the treatment (e.g., presence of fluid within the patient 350, location of the catheter). Additionally or alternatively, the interacting element 300 may provide a stimulus (e.g., mechanical stimulus, a thermal stimulus, an acoustic pressure stimulus, an electromagnetic stimulus, a chemical stimulus, and an electrical stimulus) to the vein in which the catheter 200 is inserted, to the catheter 200, and/or to the patient's body surrounding the vein, for example, to pulse the catheter 200 to prevent biofilm or fibrin build-up (discussed in greater detail below).

It should be noted that, although FIGS. 1 and 2 show a physical form for the receptacle 150 for receiving the interacting element 300, other embodiments may have a physical void-based receptacle 150. For example, as shown in FIGS. 3A-3D, the device 100 may merely include a cut-out within the substrate 110 where the interacting element 300 may be received within and thus, located relative to the device 100/substrate 110. In such embodiments, a surface of the interacting element 300 may be placed on the skin of the patient 350 within the substrate 110 cut-out but it would not be physically connected to the substrate 110.

In some embodiments, the interacting element 300 may be a stand-alone component that connects and disconnects from the device 100 and may be re-used with other patients in accordance with applicable healthcare protocols. In such embodiments, the interacting element 300 may be powered by a power source that is external from the device 100 (e.g., the cable 310 of the interacting element 300 may be connected to a separate power source and/or medical equipment) (see FIG. 4A). Alternatively, the interacting element 300 may connect to the electronics located on the device 100 (discussed in greater detail below) and be powered by the device's power source (e.g., a battery 160 that may be located on or installed into the device 100) via a connection port 170. The connection between the cable 310 and the connection port 170 may be permanent (e.g., the interacting element 300 may not be reused within another device 100) or the connection may be temporary (the cable 310 can be connected and disconnected from the connection port 170) to allow the interacting element 300 to be reused.

It should be noted that the battery 160 may be integral to the device 100 and may be rechargeable. Alternatively, the battery 160 may be removable and replaceable as needed. In such embodiments, the device 100 may have a battery slot 162 into which the battery 160 may be inserted. Additionally, if the battery 160 is pre-installed into the device 160 (e.g., if the user does not install the battery 160 just prior to use), the device 160 may include a film layer that separates the contacts on the battery 160 from the contacts on the device 100. The user may then pull out the film layer prior to use to electrically connect the battery 160 to the device 100. In some embodiments, the battery 160 may be a flexible battery that is able to flex with the substrate 110 to confirm to the patient 350.

Located between the proximal portion 112 and the distal portion 116, the substrate 110 may have an intermediate portion 118. The intermediate portion 118 of the substrate 110 may space the proximal portion 112 and the distal portion 116 of the substrate 110 a known distance from each other and, in some embodiments, axially align the proximal portion 112 and distal portion 116 with each other along the length of the catheter 200. This, in turn, may position the various components of the device 100 (e.g., the stabilizer 130, the receptacle 150, the interacting element 300, etc.) at various known points along the catheter 200 (e.g., the interacting element 300 may be positioned at the catheter tip).

The substrate 110 (e.g., the intermediate portion 118) may have a dielectric portion that includes printed electronics and/or surface mounted elements that may be used to monitor and/or otherwise facilitate the monitoring of the patient 350 (e.g., an event in the body) and/or IV therapy. For example, in one application, the substrate 110 may include two temperature sensors 410/420 located/positioned to be along the length of the catheter 200 and/or vein when it is inserted into the body. In such applications, the first temperature sensor 410 may be located at the insertion site

Figure 6:
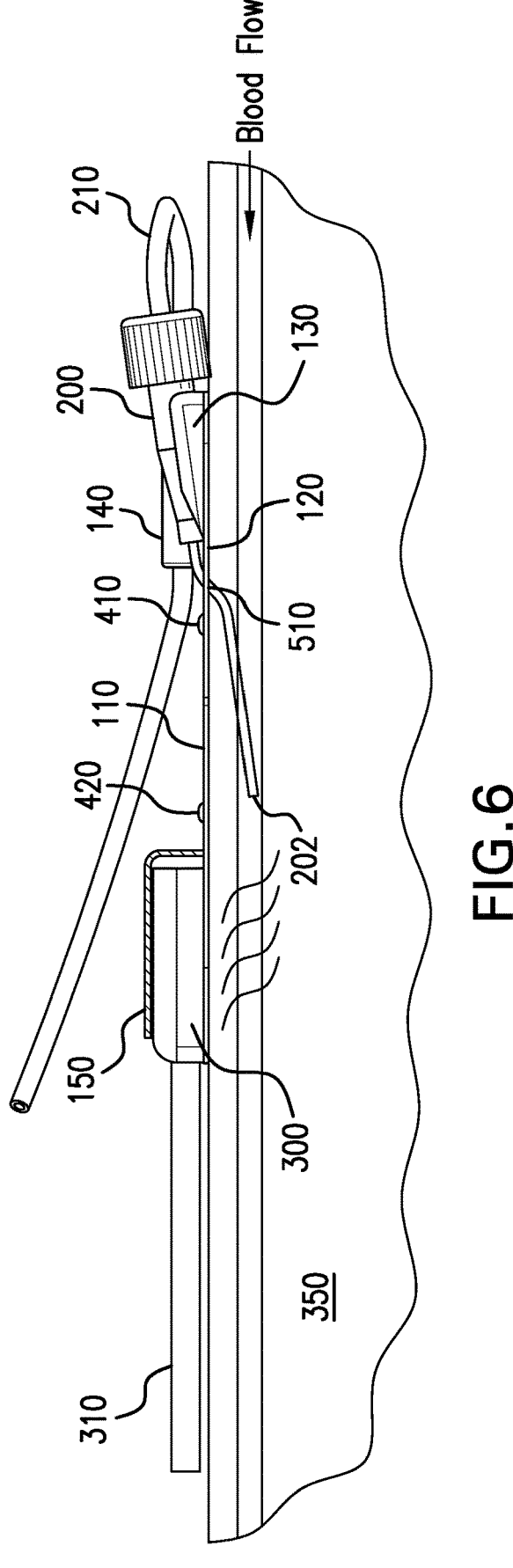
FIG. 6 schematically shows a cross-sectional view of the IV catheter stabilization and interrogation device located on the patient, in accordance with some embodiments of the present invention.

510 of the catheter 200 and the second temperature sensor 420 may be located at the catheter tip 202 (see FIG. 6). The temperature sensors 410/420 may measure the temperatures at their respective locations and, depending on the temperature profile between the two sensors 410/420, the device 100 and/or the user may be able to determine if the catheter 200 is inserted properly, whether the IV therapy is being delivered properly, etc. Additionally or alternatively, the device 110 may be able to determine if there is infiltration/extravasation of fluid, catheter dislodgment from the vein, phlebitis, local infection, systemic infection, and/or blockage of flow. To allow for remote monitoring, analysis and/or storage of the data received by the device 100 (e.g., the temperature sensors 410/420), the device 100 may also have an antenna 430 (e.g. a Bluetooth antenna) that allows the device to send the data/information to a remote device/receiver 440 (e.g., a smart phone, tablet, or computer) (FIG. 7), that, in turn, may display and/or store the data/information.

To facilitate communication between the various electrical components on the device 100 and provide power to each of these components (e.g., via the battery 160), the substrate 110 may have electrical traces 450 printed on one or both sides of the substrate 110 and connecting the various components. For example, the substrate 110 may include electrical traces 450 that connect the antenna 430 and temperature sensors 410/420 to the battery and electrical traces 450 connecting the antenna 430 to the temperature sensors 410/420. It should be noted that, although an antenna 430 and temperature sensors 410/420 are discussed above, various embodiments may have additional components as needed depending on the application for the device 100. Additionally, the device 100 may include resistors, capacitors, processors, and inductors as needed.

It should be noted that the substrate 110 may be a single layer and/or may include multiple layers and/or may be made from polyimide, polyethylene terephthalate (PET), thermoplastic polyurethane (TPU), or other suitable material. The components may be additively added by using a variety of processes such as inkjet, selective coating, screen printing, dispensing, transfer, lamination, curing, and/or subtractively tuned following traditional PCB manufacturing processes such as masking, etching, and the like, either as a sheet to sheet or as a roll to roll process. Similarly, the electrical traces can be additively added by using a variety of processes such as inkjet, selective coating, screen printing, dispensing, transfer, lamination, curing, or subtractively added following traditional PCB manufacturing processes such as masking, etching, and the like either as a sheet to sheet or as a roll to roll process.

In some instances/applications, the device 100 may require some surface mounted components such as LEDs, photodiodes, etc. Such components can be attached using solder, conductive adhesive, anisotropic conductive film (ACF), wire bonding, thermosonic bonding that is deposited by printing, inkjet, selective coating, screen printing, dispensing, lamination, curing, and/or bonding.

Figure 5:
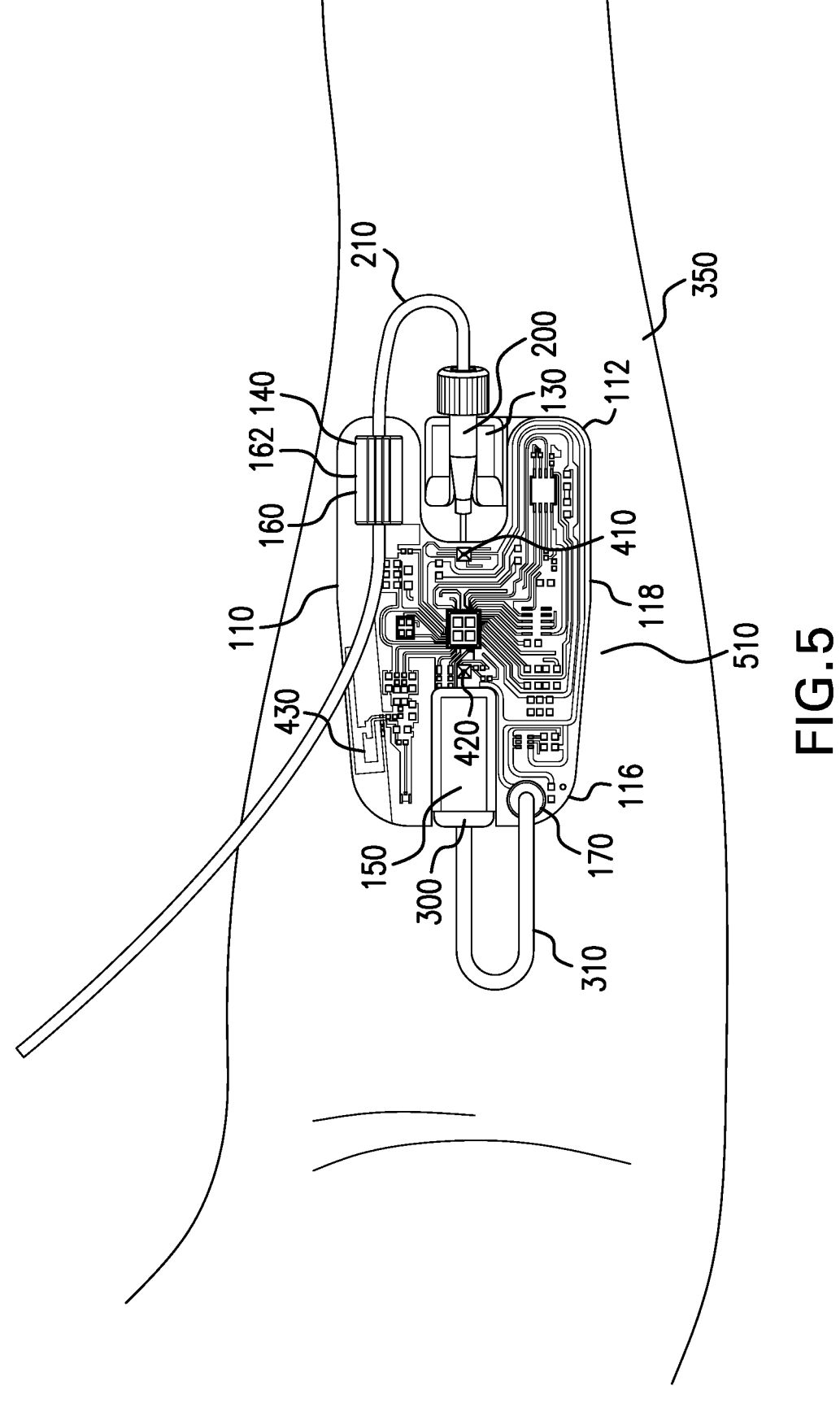
FIG. 5 schematically show the IV catheter stabilization and interrogation device of FIG. 4B located on a patient, in accordance with various embodiments of the present invention.

During use, the user/technician may first insert the catheter into the patient's vasculature at the desired location (e.g., arm, hand). Once the catheter is in place, the user may remove the protective layer covering the adhesive (if equipped) and then place the device 100 over the catheter insertion site 510 (FIGS. 5, 6, and 7) such that the catheter 200 extends through the opening 114 within the substrate 110. The user my then insert the catheter 200 into the stabilizer 130 to secure and stabilize the catheter 200 and, perhaps, set the angle of the catheter 200 relative to the patient/patient's vasculature. Alternatively, the catheter 200 may be attached to the stabilizer 130 prior to securing the device 100 to the patient 350. If the tubing line 210 is already attached to the catheter 200, the user may also secure the tubing line 210 within the tube clip 140 to secure the tubing line 210 in place. As noted above, the substrate 110 may be flexible, therefore, once placed on the patient 350, the substrate 110 will conform to the patient 350 and the adhesive will secure the device 100 to the patient 350. The user may also position the interacting element 300 within the receptacle 150.

Figure 7:
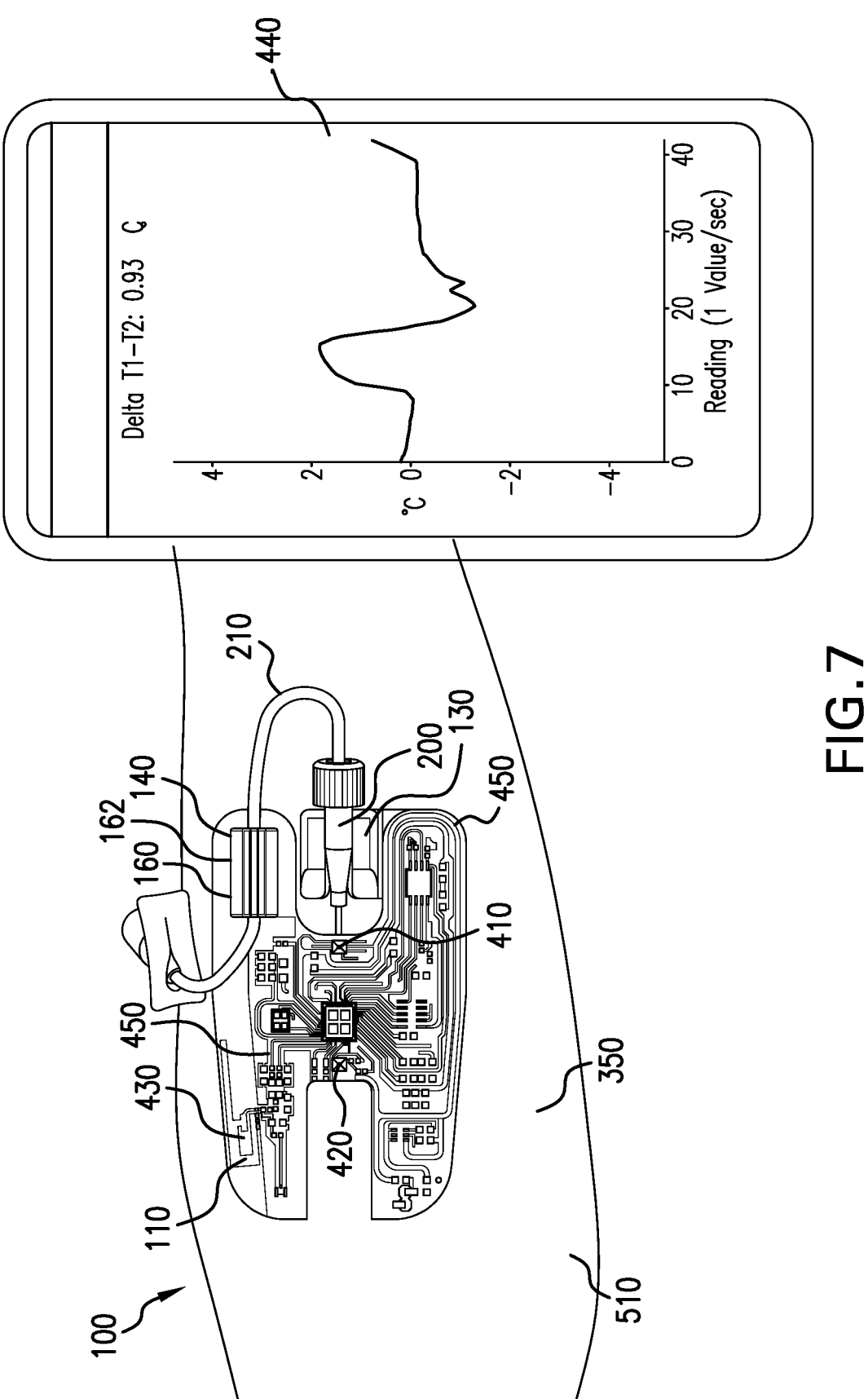
FIG. 7 schematically shows an IV catheter stabilization and interrogation device located on the patient and communicating with a remote device, in accordance with embodiments of the present invention.

Once the device 100 is secured to the patient 350 and the catheter 200 is connected to the stabilizer 130, the device 100 may then begin to monitor the patient 350 (e.g., one of the events described above). For example, if the device 100 is equipped with the temperature sensors 410/420 discussed above, the temperature sensors 410/420 may monitor the temperatures at their respective locations along the length of the catheter 200 (e.g., at the insertion site 510 of the catheter 200 and the tip 202 of the catheter 200). The data collected from the temperature sensors 410/420 may then be communicated to the antenna 430 and then sent via the antenna 430 to the remote device 440 (FIG. 7). In this manner the device 100 allows the remote device 440 and/or the doctor/technician to monitor and analyze the temperature data and the IV therapy to ensure that there is no infiltration/extravasation of fluid, the catheter has not dislodged from the vein, there is no blockage of flow and that the patient 350 is not suffering from phlebitis and/or local or systemic infection.

After the catheter 200 has been inserted in the patient 350 for a period of time, bio-film and/or fibrin may begin to build up at or upon the catheter 200. This build-up can negatively impact the performance of the catheter 200 and may otherwise cause issues such as infection. To help prevent the build-up of fibrin and/or biofilm, the interacting element 300 that is positioned within the receptacle 150 on the device 100 may provide a stimulus (e.g., an energy based stimulus) to the patient 350 and/or near the insertion site 510. For example, the interacting element 300 may provide a mechanical, thermal, acoustic pressure, electromagnetic, chemical, and/or electrical stimulus to help breakdown the fibrin/bio-film build and help prevent additional build-up.

Although the above description discusses using the device 100 to monitor temperature, other embodiments may monitor other characteristics of the patient 350. For example, other embodiments may include oxygen sensors that measure the oxygen level of the blood within the patient's vasculature and/or any other type of sensor that may externally monitor an event within the patient 350. Similarly, the interacting element 300 need not be a sensor probe and/or provide a stimulus to the patient 350. Rather, depending on the application, the interacting element 300 may supply a substance to the skin of the patient 350 or shine an ultraviolet light on the patient 350 to help the sensors (e.g., the temperature sensors 410/420 or oxygen sensors, etc.) monitor the characteristic of the patient 350. Furthermore, other embodiments may include sensors and/or interacting elements that physically enter the patient's skin to monitor, stimulate, and/or treat the area surrounding the device 100.

The embodiments of the invention described above are intended to be merely exemplary; numerous variations and modifications will be apparent to those skilled in the art. All such variations and modifications are intended to be within the scope of the present invention as defined in any appended claims.

8

What is claimed is:

1. A catheter stabilization and interrogation device for interrogating a patient having a catheter within a vein, the device comprising:
   a flexible substrate having a proximal portion, a distal portion spaced from the proximal portion, and an intermediate portion located, at least partially, between the proximal portion and the distal portion and configured to conform to the patient's body, a bottom surface of the substrate having an adhesive configured to secure the device to the patient;
   a stabilizer secured to the proximal portion, the stabilizer configured to stabilize the catheter relative to the patient's vasculature when the device is secured to the patient;
   an interacting element configured to directly stimulate the vein in which the catheter is inserted, the catheter, and/or the patient's body surrounding the vein;
   a receptacle located within and/or upon the distal portion of the substrate, the receptacle positioned distal to the stabilizer and configured to receive the interacting element and position the interacting element upon the patient adjacent the catheter tip; and
   a monitoring device constructed within at least the intermediate portion and configured to monitor at least one event within the patient.

2. A catheter stabilization and interrogation device according to claim 1, wherein the at least one event within the patient includes at least one selected from the group consisting of IV therapy, infiltration/extravasation of fluid, catheter dislodgment from the vein, phlebitis, local infection, systemic infection, and blockage of flow.

3. A catheter stabilization and interrogation device according to claim 1, wherein the at least one event is along a length of and/or adjacent to the catheter.

4. A catheter stabilization and interrogation device according to claim 1, further comprising a tube clip located within the proximal portion and configured to secure a tube from a connector set connected to the catheter.

5. A catheter stabilization and interrogation device according to claim 1, wherein the stabilizer receives at least a portion of the catheter, thereby stabilizing the catheter and/or sets an angle of the catheter relative to the patient.

6. A catheter stabilization and interrogation device according to claim 1, wherein the proximal portion and/or the distal portion is axially aligned with the catheter.

7. A catheter stabilization and interrogation device according to claim 1, wherein the intermediate portion is a dielectric portion having electronics printed and/or mounted thereon.

8. A catheter stabilization and interrogation device according to claim 7, wherein the electronics includes a first temperature sensor located nearer the proximal portion and a second temperature sensor located nearer the distal portion, the first temperature sensor configured to monitor a first temperature at a first point along a length of the catheter, the second temperature sensor configured to monitor a second temperature at a second point along the length of the catheter.

9. A catheter stabilization and interrogation device according to claim 8, wherein the first point along the length of the catheter is at an insertion site of the catheter and the second point along the length of the catheter is at the tip of the catheter.

10. A catheter stabilization and interrogation device according to claim 7, wherein the electronics includes an antenna.

11. A catheter stabilization and interrogation device according to claim 1, wherein the interacting element is a sensor probe.

12. A catheter stabilization and interrogation device according to claim 1, wherein the interacting element is configured to directly stimulate the vein in which the catheter is inserted, the catheter and/or the patient's body surrounding the vein by providing at least one selected from the group consisting of a mechanical stimulus, a thermal stimulus, an acoustic pressure stimulus, an electromagnetic stimulus, a chemical stimulus, and an electrical stimulus.

13. A method for monitoring at least one event within a body of a patient comprising:

providing a catheter stabilization and interrogation device for interrogating a patient having a catheter within a vein, the catheter stabilization and interrogation device including:

a flexible substrate having a proximal portion, a distal portion spaced from the proximal portion, and an intermediate portion located, at least partially, between the proximal portion and the distal portion and configured to conform to a patient's body, a bottom surface of the substrate having an adhesive configured to secure the device to a patient, a stabilizer secured to the proximal portion, the stabilizer configured to stabilize the catheter relative to the patient's vasculature when the device is secured to the patient, a receptacle located within and/or upon the distal portion of the substrate, the receptacle positioned distal to the stabilizer and configured to receive an interacting element and position the interacting element upon the patient adjacent the catheter tip, the interacting element configured to directly stimulate the vein in which the catheter is inserted, the catheter, and/or the patient's body surrounding the vein, and a monitoring device constructed within at least the intermediate portion and configured to monitor at least one event within the patient;

placing the catheter stabilization and interrogation device on the patient, the adhesive securing the device to the patient;

connecting the catheter to the stabilizer, the stabilizer stabilizing the catheter relative to the patient's vasculature;

positioning the interacting element within the receptacle; and monitoring the at least one event within the patient.

14. A method according to claim 13, wherein the intermediate portion is a dielectric portion with printed and/or mounted electronics thereon, the electronics including a first temperature sensor located nearer the proximal portion and a second temperature sensor located nearer the distal end, monitoring the at least one event including monitoring, using the first temperature sensor, a first temperature at a first point along a length of the catheter, and monitoring, using the second temperature sensor, a second temperature at a second point along the length of the catheter.

15. A method according to claim 14, wherein the first point is at an insertion site of the catheter and the second point is at the tip of the catheter.

16. A method according to claim 13, wherein the interacting element is a sensor probe.

17. A method according to claim 13, wherein the at least one event is along a length of and/or adjacent to the catheter.

18. A method according to claim 13 further comprising:

sending, using an antenna located on the catheter stabilization and interrogation device, data from the monitoring device to a remote device.

19. A method according to claim 13, wherein the stabilizer sets an angle of the catheter relative to the patient.

* * * * *